United States Patent [19]

Grimshaw et al.

[11] Patent Number: 4,663,081

[45] Date of Patent: May 5, 1987

[54] LIQUID PERFUME COMPOSITION

[75] Inventors: Bryan Grimshaw, Essex; Timothy S. Whiteley, London, both of England

[73] Assignee: Bush Boake Allen Limited, London, England

[21] Appl. No.: 825,052

[22] Filed: Jan. 31, 1986

[30] Foreign Application Priority Data

Jan. 31, 1985 [GB] United Kingdom ................. 8502395

[51] Int. Cl.$^4$ ............................................... A61K 7/46
[52] U.S. Cl. .................................... 252/522 R; 239/44
[58] Field of Search ........................ 239/44; 252/522 R

[56] References Cited

U.S. PATENT DOCUMENTS 3,945,950  3/1976  Vosganiantz ................... 252/522 A Primary Examiner—Bernard Helfin
Attorney, Agent, or Firm—Kane, Dalsimer, Kane, Sullivan and Kurucz

[57] ABSTRACT

A liquid composition, suitable for use in an air freshener, comprising a vessel for the composition, an emanating surface and a wick for supplying the liquid to the emanating surface, contains 20 to 70% water, 8 to 30% perfume and diethylene glycol monobutyl ether and is substantially free of surface active agent. The compositions show an improved, steady rate of emanation of the perfume.

6 Claims, 2 Drawing Figures

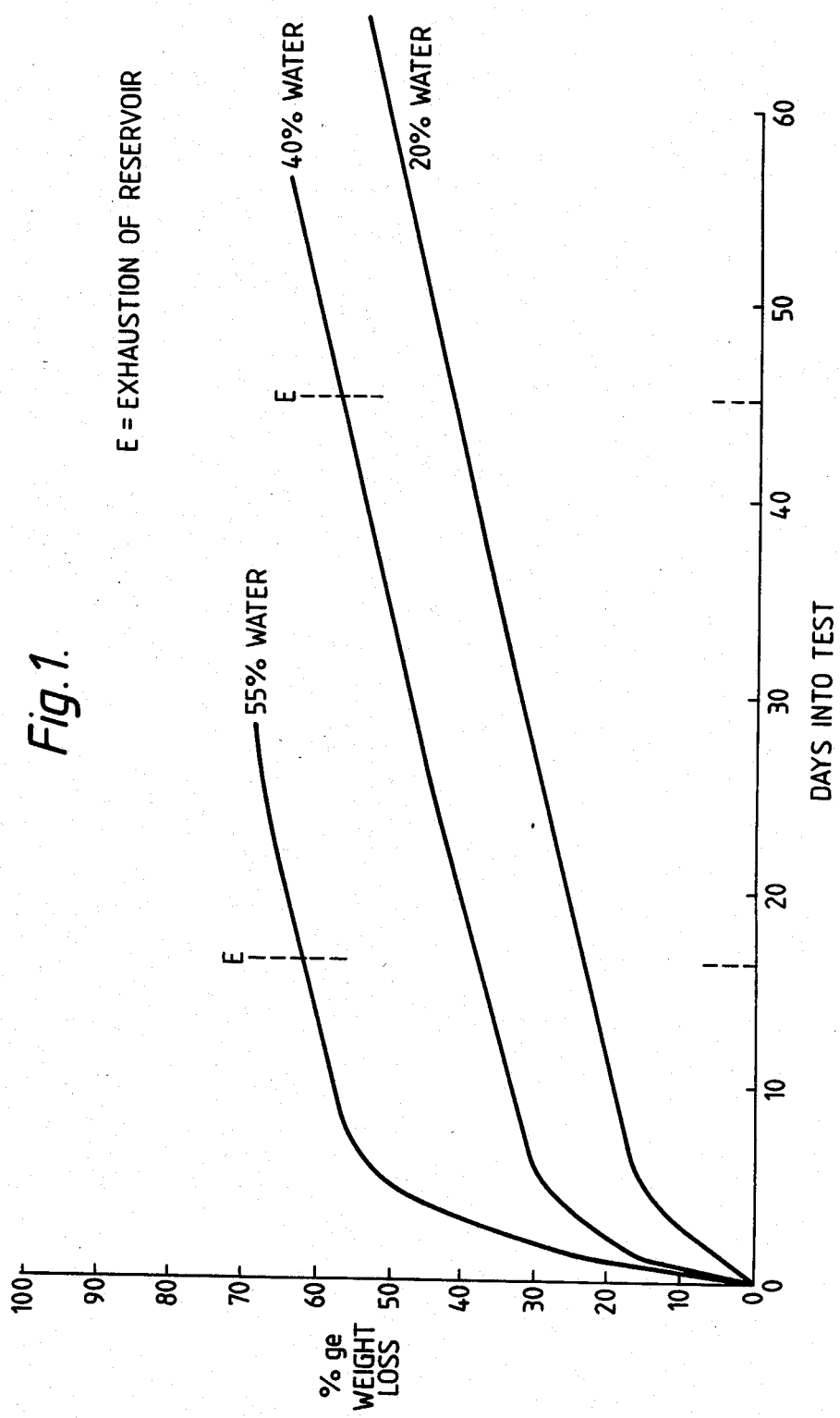

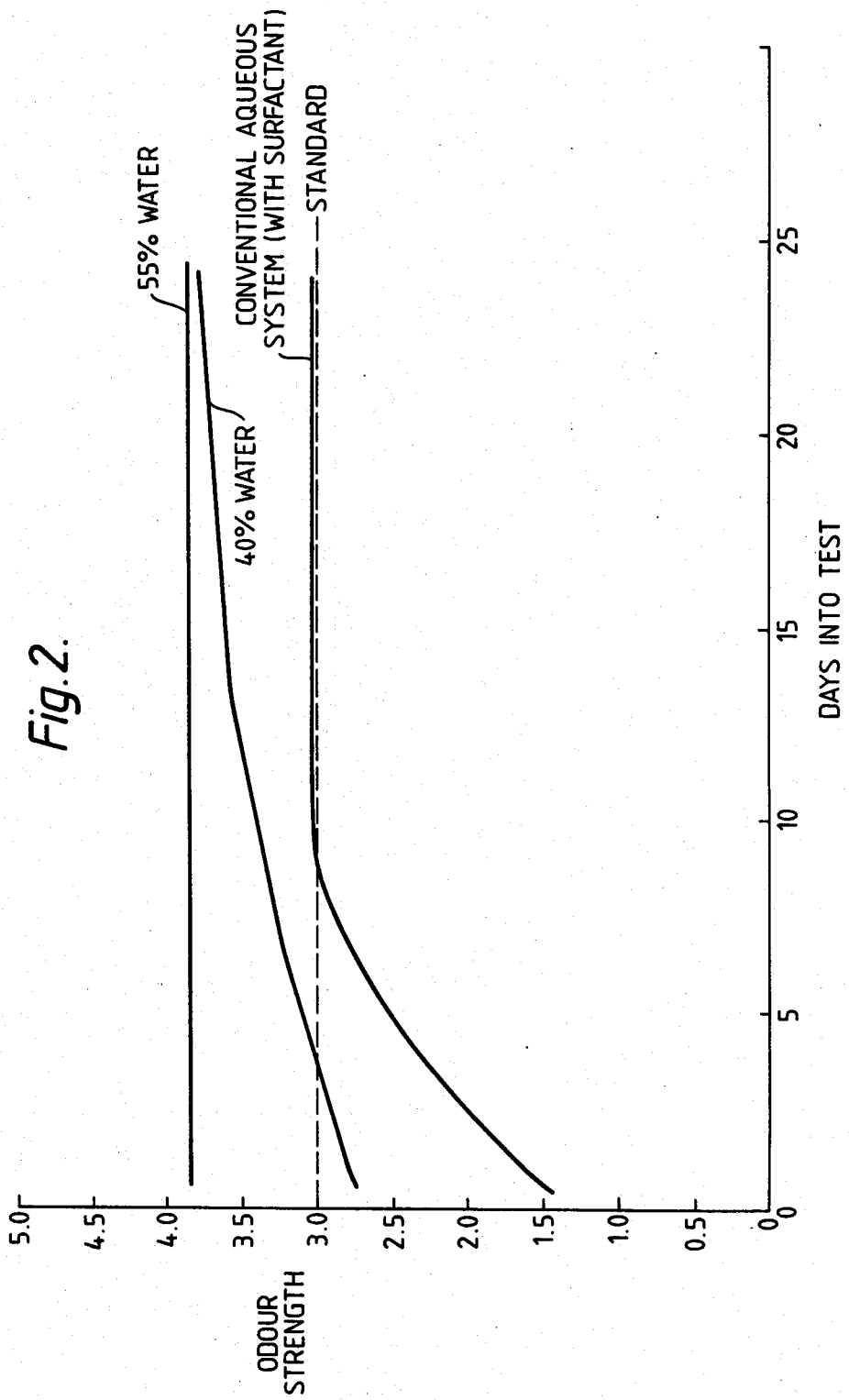

LIQUID PERFUME COMPOSITION

This invention relates to liquid compositions for use in air fresheners and to air fresheners comprising such compositions.

Conventional liquid air fresheners generally comprise a reservoir containing a mixture, which may be a true solution, a colloidal solution or a microemulsion, of a perfume with a solvent into which dips a wick which is connected to an emanating surface. The perfume mixture travels up the wick to the emanating surface from which the perfume evaporates and freshens the surrounding atmosphere. Perfumes used in these air fresheners are generally oils and are therefore generally insoluble in water in the absence of any other agents. Systems in which the perfume solution is aqueous based therefore always contain a surface active agent which solubilises the perfume in water. The amount of surfactant generally has to be quite high, for instance 10 to 15% or more, by weight based on the total composition.

The surfactants used in such compositions are conventional surfactants, generally anionic surfactants, such as alkyl benzene sulphonates and lauryl sulphates. Non-ionic surfactants have also been used, but they are more expensive and tend to depress the perception of the perfume odour. These surface active agents are all involatile, and they therefore do not evaporate from the emanating surface. The concentration of surfactant in the emanating surface therefore gradually increases and the presence of surfactant impedes the progress of perfume in the wick and also prevents the perfume emanating as it should.

Most aqueous based systems also contain a cosolvent in addition to the perfume and surfactant. Examples of cosolvents are ethanol and diethylene glycol monoethyl ethers (DEGMEE). Such compositions always contain a surfactant and therefore suffer the same disadvantages as described above.

Some liquid air fresheners contain little or no water and so are free of surfactant. For instance, a solution of perfume in DEGMEE and water is stable as a single phase provided the amount of water is low, for example below 20% when the amount of perfume is about 10% by weight. Since these compositions cannot tolerate high amounts of water, they tend to be expensive.

U.S. Pat. No. 3,945,950 describes solid air freshener compositions, which suffer from different problems to the air fresheners comprising liquid compositions with which the present invention is concerned. The solid compositions contain perfume, a diethylene glycol monoalkyl ether and a gelling agent, which is a surface active fatty acid soap or metal salt thereof, and an inert liquid. Water is sometimes included in the compositions as some or all of the inert liquid, but only in small amounts of 4% by weight.

Although DEGMBE is mentioned in the specification, it is clear that DEGMEE is the preferred ether in the solid compositions described.

We have tested other glycol ethers and have found in general that ethers which are more volatile than DEGMEE and the perfume evaporate very quickly and leave a relatively large amount of perfume in the wick when the liquid reservoir is exhausted. The point at which the liquid reservoir is exhausted is a signal to the consumer either to dispose of the air freshener, in which case the perfume left in the wick is wasted, or, if the consumer still perceives at least some odour, then he will retain the air freshener even though it no longer shows optimum odour characteristics. It is desirable for a relatively small amount of perfume to be left in the wick at exhaustion in order that the consumer disposes of the air freshener shortly thereafter thereby wasting little of the perfume. For example an aqueous propylene glycol mono-methyl ether system containing 20% of water and 10% of perfume shows poor characteristics, in that after six days, the composition on the wick contains 30% perfume and only 50% of solvent, indicating that the solvent is evaporating fast whilst the perfume is evaporating comparatively slowly. Additionally the odour characteristics of air fresheners of that composition are poor compared to standard air fresheners. Similar results are obtained with propylene glycol monoethyl ether and ethoxy ethanol, the latter also being toxicologically unacceptable.

Glycol ethers having a much lower volatility than DEGMEE and perfume generally tend to evaporate slowly and to depress the rate of emanation of the perfume thereby lowering the odour perception of the air freshener and prolonging its life undesirably.

Glycol ethers having mid-range volatility, such as the acetates of propylene glycol mono-ethyl ether or propylene glycol mono-ethyl ether will tolerate only very small amounts of water for example less than 10%.

Diethylene glycol monobutyl ether (DEGMBE) has a low volatility relative to conventional air freshener perfumes and was therefore expected to be unsuitable for use a aqueous based liquid air fresheners. It is surprising that when mixed with water and perfume it forms a solution having very desirable properties.

A composition suitable for use in a liquid air freshener comprises water, diethylene glycol monobutyl ether and perfume. A particular advantage of the composition in accordance with the invention is that they can easily be formulated as a stable one-phase mixture that contains very small amounts of surfactant or is completely free of surfactant. Since the compositions according to the invention contain lower proportions of surfactant than conventional aqueous based air freshener systems, they do not suffer from the same problems of clogging of the wick. Preferably the amount of surfactant is less than 5% by weight, more preferably less than 2%, but generally the compositions are free of surfactant.

We have found that diethylene glycol monobutyl ether (DEGMBE) can, when containing dissolved perfume, incorporate a surprisingly large amount of water compared to other glycol ethers and is therefore more cost effective. The mixture of DEGMBE and water also has very suitable volatility properties and has a beneficial effect on the rate of emanation of the perfume.

The composition generally comprises between 5 and 30% by weight of perfume. Usually the concentration of perfume is between 8 and 20% by weight, often about 10% by weight.

The amounts of perfume in compositions containing DEGMBE affect the amount of water that can be mixed into the solution before a phase separation occurs. For example when the concentration of perfume in the solution is 10% by weight then the maximum amount of water that can be incorporated in a one phase solution is about 55% by weight. For a perfume solution at 20% concentration the maximum amount of water is about 40% by weight, and for 30% perfume the maximum amount of water is about 25% by weight. The amount of DEGMBE in the composition is therefore generally in the range 30 to 50%, although higher amounts can be used if desired.

Generally the amount of water is from 50 to 100%, preferably 75 to 100%, of the maximum amount of water that can be added before a phase separation of the mixture occurs. Increasing the amount of water towards 100% of that maximum increases the initial rate of emanation of the perfume and therefore improves the early reaction of the consumer to the air freshener. Lower amounts of water tend to reduce the initial rate of emanation but tend to lead to a reduction in the amount of perfume left in the wick when the liquid reservoir is exhausted, which is desirable for the reasons mentioned above. A suitable balance of these two properties is attained when the amount of water is between 80 and 95% of the maximum. For composition comprising 10% by weight of perfume the amount of water is usually between 40 and 55% by weight, preferably between 45 and 50% by weight.

The perfume may be any of the perfumes conventionally used in air fresheners, the identity of the perfume making little difference to the behaviour of the solvent system.

The composition according to the invention is useful in any type of air freshener which consists of an emanator surface to which perfume solution may be supplied via a wick which is attached to the eminator and which dips into the liquid reservoir. Generally the air freshener apparatus comprises a cover which may be placed over the emanator surface to close it from the atmosphere either partially or completely. It has been found that the emanator surface and the wick are conveniently formed of an integral strip of cellulosic material, for instance paper which is absorbent. Such a strip of paper may have narrow regions, which form the wick, and broader areas, which form the emanator surface. The strip of paper is folded into the desired configuration such that the wick can dip into the reservoir of perfume solution in a container and the emanator surface protrudes from the container.

The air freshener of the present invention is generally formulated such that the life before the reservoir is exhausted is more than 14 days, generally less than 60 days and usually approximately 30 days.

The following examples illustrate the invention and in these Examples reference is made to the accompanying drawings, in which:

FIG. 1 shows the relative rates of emanation of compositions according to the invention containing differing amounts of water over a period of time;

FIG. 2 shows the odour characteristics of two compositions according to the invention containing differing amounts of water compared to a conventional aqueous based air freshener over a period of time;

EXAMPLE 1 demonstrates the tolerance of various perfume in glycol ether solutions to water.

Solutions of perfume in various glycol ethers of varying concentration were loaded with water until phase separation occurred. The maximum amounts of water tolerated in systems at various perfume concentrations for the glycol ethers tested is shown in Table 1.

TABLE 1

Maximum amount of water that can be incorporated into the perfume/glycol ether mixtures, before phase separation

| GLYCOL ETHER | % PERFUME IN MIXTURE | | | | |
| --- | --- | --- | --- | --- | --- |
|  | 10 | 20 | 30 | 40 | 50 |
| PGMBE | 10 | — | — | — | — |

TABLE 1-continued

Maximum amount of water that can be incorporated into the perfume/glycol ether mixtures, before phase separation

| GLYCOL ETHER | % PERFUME IN MIXTURE | | | | |
| --- | --- | --- | --- | --- | --- |
|  | 10 | 20 | 30 | 40 | 50 |
| DEGMEE | 15 | 10 | 10 | 10 | — |
| DEGDME | 20 | 10 | — | — | — |
| TPGMME | 20 | 10 | 10 | — | — |
| PGMPE | 20 | 10 | 10 | — | — |
| PGMME | 20 | 10 | 10 | 10 | — |
| DPGMME | 20 | 20 | 10 | 10 | — |
| PGMEE | 30 | 20 | 10 | 10 | — |
| DEGMBE | 60 | 40 | 20 | 20 | 10 |

As can be seen from the table DEGMBE can tolerate a far larger amount of water at a specified perfume concentration than any of the other glycol ethers.

EXAMPLE 2

Solutions containing 10% by weight perfume and differing amounts of DEGMBE and water were made up and 50 grams of the solutions placed in conventional air freshener apparatus. The rate of emanation of the solution was measured over a 60 day period by measuring the percentage of weight loss over the period up to exhaustion of the reservoir or the end of 60 days as appropriate.

The results are shown in the accompanying graph, FIG. 1, which shows that a steady rate of emanation is reached after about 7 days in each case, and that the rate of emanation in those 7 days depends on the initial amount of water. That is, the more water the faster is the initial rate of emanation. The steady state rate of emanation is approximately the same in each case, and therefore the life of the high water containing system is much shorter than the lower water system. The graph shows that the amount of perfume solution left in the wick at exhaustion of the reservoir also varies with the amount of water in the solution. That is, the lower water systems have a relatively larger amount of solution left in the wick at exhaustion of the reservoir.

The amount of solution left in the wick at exhaustion should be as low as possible for economic reasons.

EXAMPLE 3

The wicks at exhaustion in Example 2 were analysed to determine the amounts of each component left at that time. The proportion of the total amount of perfume in the reservoir at the start that has emanated for the three compositions is shown in the accompanying Table 2.

TABLE 2

| Concentration water % w/w. | Exhaustion days | Perfume emanated (% of original) |
| --- | --- | --- |
| 20 | >>60 | >75% |
| 40 | 45 | 71% |
| 55 | 16 | 64% |

It can be seen from Table 2 that the lower the concentration of water the higher the proportion of perfume originally present has emanated from the wick at the points at which the reservoir is empty.

EXAMPLE 4

Perfume solutions were prepared as for Example 2 containing respectively 40% and 55% by weight water and 50 grams of the solutions were tested in air freshener apparatus against a conventional water based air freshener containing surfactant. The air fresheners were tested over a 30 day period for their odour characteristics. Values were given for each air freshener on a scale of 1 (poor) to 5 (excellent) in comparison with a standard odour strength given a nominal value of 3. The results are shown in graph FIG. 2.

The 40% water system containing DEGMBE shows better characteristics than the standard after the first 3 or 4 days and the 55% water has better characteristics than standard from the start of the test. In contrast the conventional aqueous base system containing surfactant is very poor compared to the standard for at least the first 10 days and only average thereafter.

We claim:

1. A liquid air freshener composition comprising water, diethylene glycol monobutyl ether and perfume which is substantially free of surface active agent.

2. A composition according to claim 1 in which the perfume is present in an amount of 5 to 30% by weight.

3. A composition according to claim 1 in which the perfume is present in an amount 8 to 20% by weight.

4. A composition according to claim 1 in which the solution comprises 20 to 70% by weight of water.

5. A composition according to claim 1 in which the solution comprises 40 to 55% by weight of water and 5 to 30% perfume.

6. A liquid air freshener composition consisting essentially of water, diethylene glycol monobutyl ether and perfume.

* * * * *